United States Patent [19]
Ukishiro et al.

[11] Patent Number: 5,784,991
[45] Date of Patent: Jul. 28, 1998

[54] METHOD FOR REARING OR TRANSPORTING ENTOMOPHAGOUS INSECT

[75] Inventors: Noboru Ukishiro; Yoshinori Shono, both of Sanda, Japan

[73] Assignee: Sumitomo Chemical Company, Limited, Osaka, Japan

[21] Appl. No.: 760,568

[22] Filed: Dec. 4, 1996

[30]  Foreign Application Priority Data

Dec. 4, 1995 [JP] Japan ................................. 7-315233

[51] Int. Cl.$^6$ .................................................. A01K 67/00
[52] U.S. Cl. .................................................. 119/6.5
[58] Field of Search ........................ 119/6.5, 6.6, 6.7; 449/27, 28

[56]  References Cited

U.S. PATENT DOCUMENTS

| | | | |
|---|---|---|---|
| 3,345,974 | 10/1967 | Phillips et al. | 119/6.5 |
| 4,192,254 | 3/1980 | Apel | 119/6.7 |
| 4,334,498 | 6/1982 | Bedding | 119/6.7 |
| 4,785,764 | 11/1988 | Muller | 119/6.5 |

FOREIGN PATENT DOCUMENTS

| | | |
|---|---|---|
| 0204999 | 5/1986 | European Pat. Off. . |
| 2050836 | 5/1980 | United Kingdom . |

OTHER PUBLICATIONS

Chinese Journal of Entomology, *Improvement of a Standard Technique for Group-Rearing Larvae of Green Lacewing*, Wen-Tai Lee, ISSN 0258-462X, vol. 15, No. 1 (Mar., 1995)(and English translation thereof).

*Primary Examiner*—Ren Yan
*Assistant Examiner*—Amanda B. Sandusky
*Attorney, Agent, or Firm*—Birch, Stewart, Kolasch & Birch, LLP

[57]  ABSTRACT

Small lumps of foamed plastic may be used as a shelter for rearing or transporting entomophagous insects. Also disclosed is a container for keeping entomophagous insects, which comprises a hollow body containing small lumps of foamed plastic and provided with one or more holes on its upper surface, the holes being of a size such that the entomophagous insects can pass through them but the small lumps of foamed plastic can not pass through them. This arrangement prevents the entomophagous insects from preying on each other, making it possible to efficiently rear or transport the entomophagous insects, particularly predatory insects such as lacewings, lady beetles and predatory bugs, for use in controlling insects that are harmful to field crops.

6 Claims, 1 Drawing Sheet

METHOD FOR REARING OR TRANSPORTING ENTOMOPHAGOUS INSECT

FIELD OF THE INVENTION

The present invention relates to a method for rearing or transporting entomophagous insects such as arthropods, particularly predatory insects, and a container for keeping the entomophagous insects.

DESCRIPTION OF THE RELATED ART

In order to control noxious insects by utilizing an entomophagous predatory insect a large number of the predatory insects have been required. These have been reared using paper, rice hulls, buckwheat husk or the like as a shelter for the purpose of preventing them from preying on each other.

However, these conventional shelters were not always satisfactory in that a large number of entomophagous insects in a small container have been lost while rearing or transporting because of their entomophagous nature. Furthermore undesirable molds are often formed in the rearing container. In addition, it is troublesome to separate the entomophagous insects from the shelter. Therefore, a further method to solve these problems has been desired.

SUMMARY OF THE INVENTION

The present invention solves the above problems in full or in part by a method for rearing or transporting entomrophagous insects, which comprises using small lumps of foamed plastic (plastic foam) as a shelter, and a container for keeping entomophagous insects, which comprises a hollow body containing small lumps of foamed plastic and provided with holes on its upper surface, the holes being of a size such that the entomophagous insects can pass through them but the small lumps of foamed plastic can not pass through them. The container is useful for transporting, and the entomophagous insects in the container can be readily scattered over field crops therefrom.

DESCRIPTION OF THE PREFERRED EMBODIMENT

The small lumps of foamed plastic to be used in the present invention are not specifically limited, and examples thereof include lumps of polystyrene foam, polyurethane foam, ABS foam, polyvinyl chloride resin foam, polyethylene foam, polypropylene foam, phenol resin foam, urea resin foam and the like. The expansion of these foamed plastics is usually about 5 to 80 times, preferably 10 to 50 times, relative to the corresponding unfoamed plastics.

The shape of the lumps of foamed plastic used in the present invention is not specifically limited, and it is preferred to use those having a sphere, disc, cylinder or cube-like shape. In case of the sphere or disc shape, it is preferred to use those having a diameter of 2 to 20 mm. In case of the cylinder shape, it is preferred to use those having a length of 5 to 30 mm and a diameter of 2 to 10 mm. In case of the cubic shape, it is preferred to use those having a width of 2 to 20 mm and a length of 2 to 20 mm.

The entomophagous insects which can be reared or transported by the method of the present invention include arthropods, which are generally predatory insects. Examples thereof include lacewings such as *Chrysopa septempunctata*, common green lacewing (*Chrysopelra carnea*), *Mallada formosana* and the like; lady beetles such as *Harmonia axyridis*, seven spotted lady beetle (*Coccinella septempunctata*), *Menochilus sexmaculatus* and the like; and predatory bugs such as *Eocanthecona furcellata*, *Andrallus spinidens* and the like.

The rearing method of the present invention is usually conducted by placing small lumps of foamed plastic as a shelter in the space used for the rearing insects, and the insects are reared according to a usual rearing method (see, for example, "Rearing Method of Insects", published by Takeshi YUSIMA, issued by Japanese Plant Protection Society).

The amount of the small lumps of foamed plastic to be used varies depending on the species of the entomophagous insect, but is normally from 10 to 90 ml (including air space between the lumps), preferably from 30 to 70 ml, per 100 ml of the rearing container.

According to a specific embodiment of the operation, two to twenty hatched larvae (per 100 ml of a rearing container) of an entomophagous arthropod insect, e.g. a predatory insect are left in the rearing container, and then eggs of Lepidoptera or Coleoptera (beetles), young larvae of Lepidoptera or aphids are introduced as the diet.

The kind of insect eggs that can be used as diet varies depending on the species of the entomophagous arthropod insect. In case of the lacewings, for example, eggs of Lepidoptera or Coleoptera (beetles) or aphids are used. In case of the lady beetles, for example, eggs or young larvae of Lepidoptera or aphids are used. In case of the predatory bugs, eggs or young larvae of Lepidoptera are used.

For transporting the entomophagous arthropod insects, for example, the container is filled with small lumps of the plastic foam, and then the arthropods and an optional host as the diet of the arthropods are put in it.

The present container comprises a hollow body provided with one or more holes, preferably a plurality of holes. The holes are so sized that the entomophagous insects can pass through them but the small lumps of foamed plastic can not pass through them, for example, holes having a diameter of 1 to 8 mm are usually advantageously used for practical application. The shape of the hollow body is not specifically limited. The holes provided on the upper surface may be, for example, covered with paper or woven or unwoven fabrics with permeability, the mesh of which is smaller than the insects in the container being reared or transported, if necessary. The container is useful not only for transportation of the entomophagous insects but also for scattering the reared insects over field crops simply by putting the holes provided on the upper surface downward and shaking the container. FIG. 1 shows an example of the container of the present invention.

The small lumps of foamed plastic and entomophagous insects are usually kept in the container. The hollow body is usually made of plastic or glass and preferably has a volume of about 200 to 1000 ml, and preferably about 100 to 1000 entomophagous insects are usually kept per one container.

EXAMPLES

The following Examples illustrate the present invention in detail but are not to be construed to limit the scope thereof.

Example 1

Polystyrene foam spheres having a diameter of about 5 mm (100 ml, volume including air space between particles) were put in a polyethylene cup having a volume of 200 ml, and then a cotton ball (diameter: 1 cm) impregnated with water was put in it. The hatched larvae of *Chrysopa sep-*

*tempunctata* were left in the polyethylene cup and eggs of Mediterranean flour moth (*Ephestia kuehniella*) were introduced as diet. The diet was supplied at an appropriate rate during the rearing. After nine days, the number of living last instar larvae was counted to determine the survival rate. An average survival rate calculated from three replications of the experiment is shown in Table 1.

An average survival rate obtained by rearing according to the same manner as that described above except for using a shelter obtained by folding a filter paper cut in a size of 4 cm×5 cm in a corrugated shape in place of the polystyrene foam (comparative plot) is also shown in Table 1.

TABLE 1

|  | Average survival rate (%) |
|---|---|
| Test plot of the present invention | 86.7 |
| Comparative plot | 46.6 |

In the test plot of the present invention, no mold was formed. In the comparative plot, however, formation of mold was observed.

Example 2

According to the same manner as that described in Example 1 except for using *Harmonia axyridis* instead of *Chrysopa septempunctata*, rearing was conducted. After 8 days, the number of living last instar larvae was counted to determine the survival rate. The results are shown in Table 2.

TABLE 2

|  | Average survival rate (%) |
|---|---|
| Test plot of the present invention | 83.3 |
| Comparative plot | 46.7 |

In the test plot of the present invention, no mold was formed. In the comparative plot, however, formation of mold was observed.

Example 3

A polyethylene bottle having a volume of 500 ml was filled with polystyrene foam spheres having a diameter of about 5 mm and one hundred second-instar larvae of *Chrysopa septempunctata* and 500 mg of eggs of Mediterranean flour moth (*Ephestia kuehniella*) were put in it, and then the bottle was transported for 48 hours at 5° C. The survival rate after transportation was not less than 90%.

Effect of the Invention

According to the rearing or transporting method of the present invention, it is possible to conduct efficient rearing and transportation of entomophagous insects. It is also possible to readily separate the entomophagous insects from the shelter. Therefore, the container of the present invention for keeping entomophagous insects can be advantageously used as is for controlling insects that are harmful to field crops.

BRIEF EXPLANATION OF THE DRAWINGS

A schematic diagram illustrating one embodiment of the container for keeping the entomophagous insects of the present invention is shown in FIG. 1.

EXPLANATION OF SYMBOLS

Figure 1:
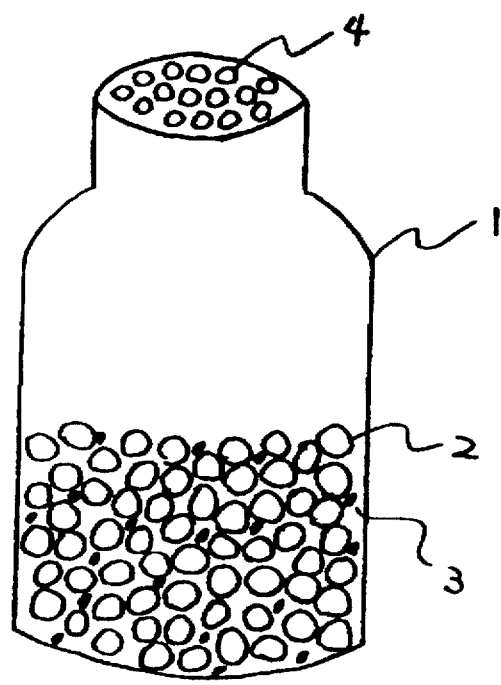

In FIG. 1, the symbol 1 represents a container for keeping entomophagous insects, 2 represents a spherical shaped foamed plastic shelter put in the container, 3 represents an entomophagous insect (predatory insect), and 4 represents a hole.

We claim:

1. A method of rearing entomophagous insects, which comprises adding entomophagous insects to small lumps of foamed plastic that acts as a shelter for said insects; and rearing said insects.

2. The method according to claim 1, wherein said small lumps of foamed plastic have a spherical shape.

3. A method of transporting entomophagous insects, which comprises adding entomophagous insects to small lumps of foamed plastic that acts as a shelter for said insects; and transporting said insects.

4. The method according to claim 3, wherein said small lumps of foamed plastic have a spherical shape.

5. In combination, a container for keeping entomophagous insects which comprises a hollow body containing small lumps of foamed plastic and provided with one or more holes on its upper surface, said holes being of a size such that the entomophagous insects can pass through said holes but wherein said small lumps of foamed plastic cannot pass through said holes; and entomophagous insects in said container.

6. The combination according to claim 5, wherein said small lumps of plastic foam have a spherical shape.

* * * * *